US00PP27457P2

(12) United States Plant Patent
Van Swieten

(10) Patent No.: US PP27,457 P2
(45) Date of Patent: Dec. 13, 2016

(54) ***PHALAENOPSIS* ORCHID PLANT NAMED 'PHALDOQAH'**

(50) Latin Name: ***Phalaenopsis* hybrid**
Varietal Denomination: PHALDOQAH

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 14/756,792

(22) Filed: Oct. 14, 2015

(51) Int. Cl.
*A01H 5/02* (2006.01)

(52) U.S. Cl.
USPC ..... Plt./311

(58) Field of Classification Search
USPC ..... Plt./311
See application file for complete search history.

(56) References Cited

PUBLICATIONS

PLUTO Plant Variety Database Sep. 10, 2016 p. 1.*
Enclosure for the Plant Patent application of Anthura BV, 13 pages, 2015.

* cited by examiner

*Primary Examiner* — Annette Para
(74) *Attorney, Agent, or Firm* — Jondle & Associates, P.C.

(57) ABSTRACT

A new and distinct variety of *Phalaenopsis* plant named 'PHALDOQAH', particularly characterized by having white flowers with stripes, 1 to 3 peduncles, an inflorescence that is long and sturdy, leaves that are obovate, and is propagated by meristem tissue culture is disclosed.

3 Drawing Sheets

Genus and species: *Phalaenopsis* hybrid.
Variety denomination: 'PHALDOQAH'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALDOQAH'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, are three-lobed and are often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALDOQAH' is particularly characterized by its attractive and unique light purple flower with stripes, economical propagation by tissue culture, rapid growth, and a plant dimension suitable for packaging and shipping to the market.

'PHALDOQAH' is a product of a planned breeding program conducted by the inventor in Bleiswijk, The Netherlands.

The new *Phalaenopsis* 'PHALDOQAH' originated from a cross made in February 2005 in Bleiswijk, The Netherlands. The female parent is a light purple striped Phalaenopsis pot plant named '12758-0002' (unpatented), while the male parent is a white striped *Phalaenopsis* pot plant named '06831-0002' (unpatented). A single plant was selected in February 2008 and has been asexually reproduced repeatedly by meristem tissue culture in Bleiswijk, The Netherlands over a 4-year period. The new variety has been found to retain its distinctive characteristics through successive asexual propagations.

Asexual reproduction of 'PHALDOQAH' by tissue culture was first performed in December 2011 in Bleiswijk, The Netherlands and has demonstrated that the new cultivar is firmly fixed and retained through successive generations of asexual reproduction.

Plant Breeder's Rights for this variety have been applied for in Europe on Sep. 29, 2014. 'PHALDOQAH' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) White flower with stripes;
2) 1 to 3 peduncles;
3) Inflorescence is long and sturdy;
4) Shape of the leaf is obovate; and
5) Plants are propagated by meristem tissue culture.

DESCRIPTION OF THE PHOTOGRAPHS

This new *Phalaenopsis* plant is illustrated by the accompanying photographs which show the overall plant habit including blooms, buds and foliage of the plant; the colors shown are as true as can be reasonably obtained by conventional photographic procedures. The photographs are of a 50-week old plant grown in a greenhouse in Bleiswijk, The Netherlands in July 2015.

DESCRIPTION OF THE NEW VARIETY

Figure 1:
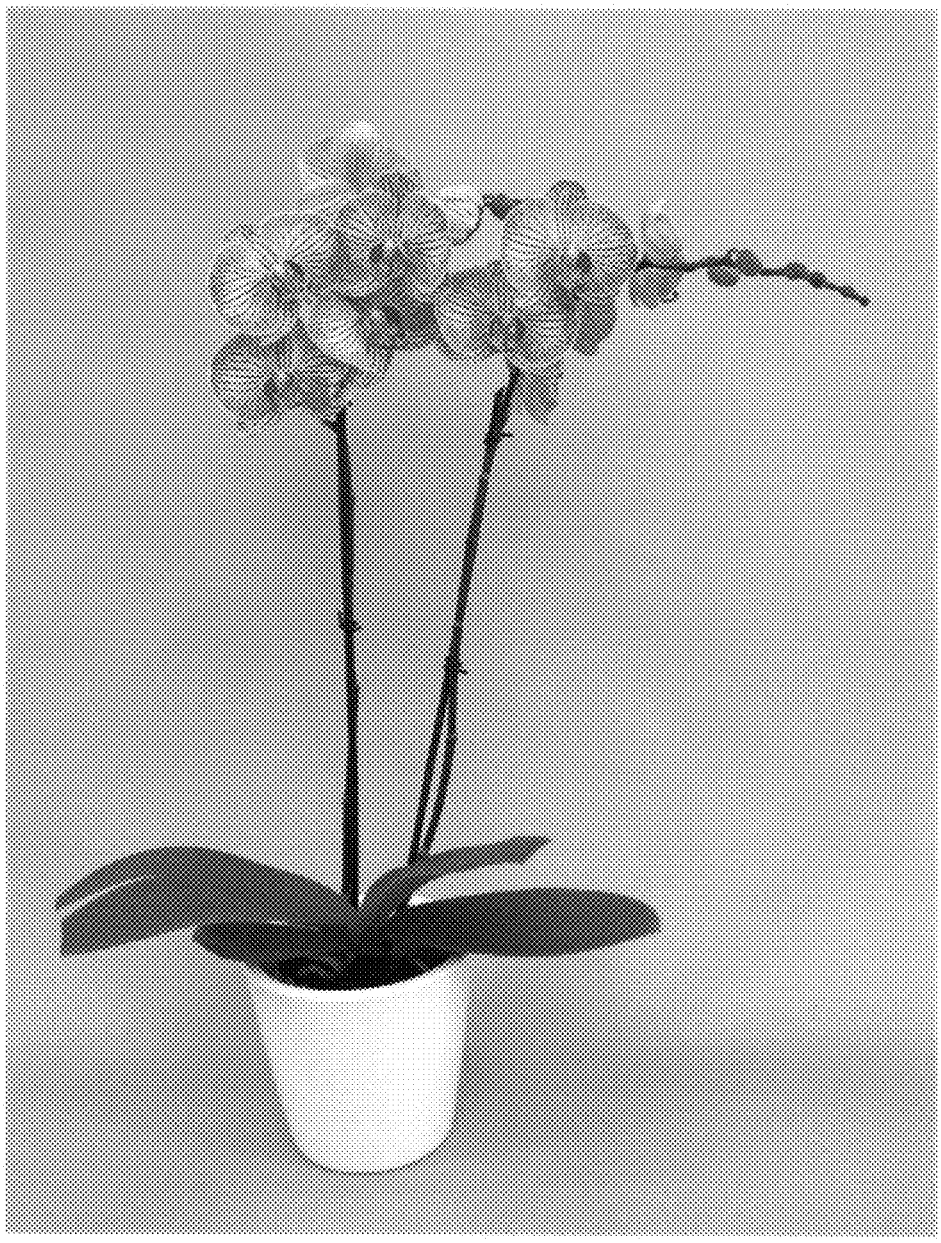
FIG. 1 shows the overall plant habit, including blooms, buds and foliage of 'PHALDOQAH'.
Figure 2:
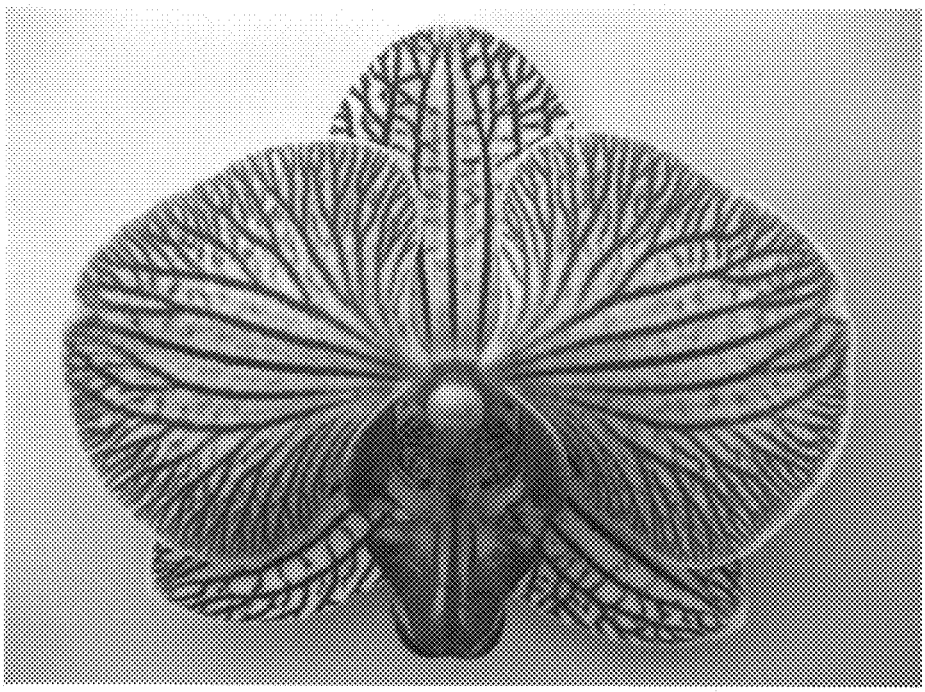
FIG. 2 shows a close-up of a flower of 'PHALDOQAH'.
Figure 3:
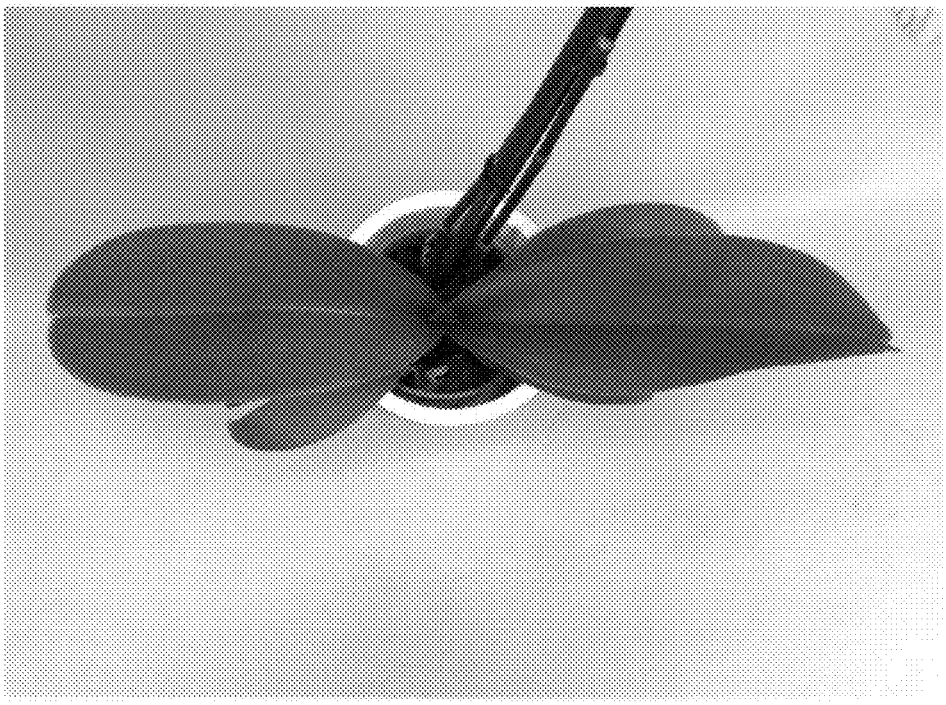
FIG. 3 shows a close-up of the leaves of 'PHALDOQAH'.

The following detailed description sets forth the distinctive characteristics of 'PHALDOQAH'. The data which define these characteristics were collected from asexual reproductions carried out in Bleiswijk, The Netherlands. The plant history was taken on 50-week old plants which were planted from a nursery tray in 12 centimeter pots and grown in a greenhouse between 27° C. to 29° C. for 30 weeks, continued by a cooling period of 8 weeks between 18° C. to 20° C. and 12 weeks in a greenhouse of 21° C. Observations were made in July 2015. Color readings were taken under 4-6000 lux natural light in the greenhouse. Color references are primarily to The R.H.S. Colour Chart of The Royal Horticultural Society of London (R.H.S.) (1995).

DETAILED BOTANICAL DESCRIPTION

Classification:
- *Family*.—Orchidaceae.
- *Botanical*.—*Phalaenopsis* hybrid.
- *Common name*.—*Phalaenopsis*.
- *Variety name*.—'PHALDOQAH'.

Parentage:
- *Female parent*.—*Phalaenopsis* cultivar '12758-0002' (unpatented).
- *Male parent*.—*Phalaenopsis* cultivar '06831-0002' (unpatented).

Propagation:
- *Type*.—Meristem tissue culture.

Plant:
- *Crop time* (*time to produce a finished flowering plant*).—48 to 50 weeks for a 12 cm pot.
- *Growth habit of peduncle*.—Standard, green leaves, raceme to panicle.
- *Height* (*including pot, including inflorescence*).—57.0 cm to 67.0 cm.
- *Width* (*measured from leaf tips*).—40.0 cm to 45.0 cm.
- *Vigor*.—Strong.

Roots:
- *Root description*.—Greyed-green colored roots with branching lateral roots having yellow-light green colored root tips.

Leaves:
- *Mature leaves*.—Quantity per plant: 6 to 8 leaves are produced before flowering. Length (fully expanded): 20.0 cm to 24.0 cm. Width: 9.5 cm to 10.5 cm. Shape: Obovate. Base shape: Very elongated. Apex: Unequal rounded. Leaf blade angle with the petiole (measured from the horizontal position): Between 0 degrees and 50 degrees. Leaf margin: Entire. Color: Upper surface: RHS 146A. Lower surface: RHS 146B. Texture: Rough. Thickness: 2.3 mm to 2.8 mm. Venation: Pattern: Parallel. Color of the midvein: Upper surface: RHS 146A. Lower surface: RHS 146B.

Peduncle:
- *Quantity per plant*.—1 to 3.
- *Number of flowers per peduncle*.—11 to 17.
- *Length*.—53.0 cm to 58.0 cm.
- *Diameter*.—5.1 mm to 5.5 mm.
- *Strength*.—Strong.
- *Aspect*.—Upright to slightly pendant.
- *Texture*.—Slightly rough.
- *Color*.—Mix of brown (RHS 200A) and green (RHS 146C).
- *Internode length*.—33.0 mm to 43.0 mm.
- *Callosities*.—None.

Inflorescence description:
- *Appearance*.—Upright to slightly pendant, raceme to panicle inflorescence with bilaterally symmetrical flowers that open in succession beginning with the lowermost flower.
- *Inflorescence size*.—Height (from base to tip): 245.0 mm to 275.0 mm. Diameter: 3.6 mm to 3.9 mm.
- *Flowering time*.—First flowers can be expected 10 to 11 months after planting in a 12 cm pot.
- *Flower*.—Height: 77.0 mm to 82 0 mm. Diameter: 89.0 mm to 94.0 mm. Depth of lip: 19.0 mm to 21.0 mm.
- *Flower longevity*.—On the plant: 11 to 13 weeks.
- *Fragrance*.—Absent.
- *Flower bud*.—Length: 22.0 mm to 24.0 mm. Width: 18.0 mm to 20.0 mm. Shape: Egg shaped. Color: Mix of green (RHS 145B to 145C) and greyed-purple (RHS 186A).
- *Petals*.—Arrangement: Open/free. Shape: Semi-circular. Apex: Emarginated asymmetric. Margin: Entire. Length (from base to tip): 42.0 mm to 44.0 mm. Width: 59.0 mm to 62.0 mm. Color (when fully opened): Upper surface: Basic color: Light purple (RHS 80C to 80D) striped and slightly netted on the edge (RHS 80A). Over color: Absent. Lower surface: Basic color: White (RHS 155C) striped and slightly netted on the edge (RHS 80A to 80B). Over color: Light purple (RHS 76D).
- *Dorsal sepal*.—Shape: Broad elliptic. Apex: Rounded symmetric. Margin: Entire. Length (from base to tip): 43.0 mm to 45.0 mm. Width: 37.0 mm to 39.0 mm. Color (when fully opened): Upper surface: Basic color: White (RHS 155C) with purple stripes and a netted edge (RHS 78A and 80B). Over color: Light purple (RHS 80B to 80C). Lower surface: Basic color: White (RHS 155C) striped (RHS 80B). Over color: Light purple (RHS 76C and 76D).
- *Lateral sepals*.—Shape: Ovate. Apex: Obtuse symmetric. Margin: Entire. Length (from base to tip): 44.0 mm to 46.0 mm. Width: 31.0 mm to 33.0 mm. Color (when fully opened): Upper surface: Basic color:

White (RHS 155C) slightly striped, netted and partially dotted towards the base (RHS 78A). Over color: Absent. Lower surface: Basic color: White (RHS 155C) slightly striped and netted (RHS 78B). Over color: Light purple (RHS 76C).

*Labellum* (*lip*).—Margin: Entire. Whiskers: Present. Length of whiskers: 19.0 mm to 21.0 mm. Color of whiskers: Dark purple (RHS 78A and 79A). Pubescence on the lip: Absent.

*Lateral lobe*.—Shape: Type V (as described in the International Union for the Protection of New Varieties of Plants (UPOV) Test Guidelines for Phalaenopsis); spatulate. Length: 20.0 mm to 22.0 mm. Width: 14.0 mm to 16.0 mm. Color: Purple (RHS 78A) and red-purple (RHS 59A to 59B) with a touch of yellow on one side (RHS 13A) and white at the base (RHS 155C).

*Apical lobe*.—Shape: Triangular. Length: 19.0 mm to 21.0 mm. Width: 19.0 mm to 21.0 mm. Color: Red-purple (RHS 60A and 78A); yellow towards the base and two white stripes in the middle (RHS 155C).

*Callus*.—Average size: Medium to large. Height: 0.6 cm to 0.8 cm. Length: 0.6 cm to 0.8 cm. Width: 0.4 cm to 0.6 cm. Color: Yellow (RHS 9A) dotted (RHS 176A).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 9.0 mm to 11.0 mm. Diameter: 5.3 mm to 5.6 mm. Color: Purple (RHS 78B) with white tip (RHS 155C).

*Pollinia*.—Quantity: 2. Size: 0.9 mm to 1.2 mm. Color: Orange (RHS 25A).

*Ovary*.—Part of the pedicel with small ribs towards the column. Length: 7.0 mm to 9.0 mm. Diameter: 2.2 mm to 2.4 mm.

*Pedicel*.—Length: 33.0 mm to 35.0 mm. Diameter: 2.8 mm to 3.0 mm. Color: From the inflorescence: mix of light purple (RHS 75C) and light green (RHS 145C and 145D) to white (RHS 155C) and light purple towards the flower.

Disease, pest, and stress resistance: No specific resistance or susceptibility observed.

Temperature tolerance: Tolerant to a low temperature of 15° C. and a high temperature of about 30° C.

COMPARISON WITH PARENTAL AND COMMERCIAL VARIETIES

'PHALDOQAH' differs from female parent plant '12758-0002' (unpatented) in that 'PHALDOQAH' has a white and purple backside of the lateral lobe, whereas '12758-0002' has a purple backside of the lateral lobe with a touch of white. Additionally, 'PHALDOQAH' has a lighter flower color and wider petals than '12758-0002'.

'PHALDOQAH' differs from male parent plant '06831-0002' (unpatented) in that 'PHALDOQAH' has a flower that is striped and has a netted edge striped, whereas '06831-0002' has a flower that is striped, dotted and has a netted edge. Additionally, 'PHALDOQAH' has whiskers with white tips, whereas '06831-0002' has whiskers with yellow tips and yellow edge.

'PHALDOQAH' differs from commercial variety 'PHALBUKAP' (U.S. Plant Pat. No. 25,445) in that 'PHALDOQAH' has petals with an emarginated apex, whereas 'PHALBUKAP' has petals with a rounded apex. Additionally, 'PHALDOQAH' has shorter whiskers and a lighter flower color than 'PHALBUKAP'.

I claim:

1. A new and distinct variety of *Phalaenopsis* plant named 'PHALDOQAH', substantially as described and illustrated herein.

* * * * *